(12) United States Patent
Asbaghi

(10) Patent No.: US 6,869,415 B2
(45) Date of Patent: Mar. 22, 2005

(54) SAFETY DEVICE FOR BLOOD COLLECTION

(75) Inventor: Hooman A. Asbaghi, Del Mar, CA (US)

(73) Assignee: Vacumate, LLC, Lexington, KY (US)

( * ) Notice: Subject to any disclaimer, the term of this patent is extended or adjusted under 35 U.S.C. 154(b) by 150 days.

(21) Appl. No.: 10/289,508

(22) Filed: Nov. 5, 2002

(65) Prior Publication Data

US 2004/0087875 A1 May 6, 2004

(51) Int. Cl.[7] .............................................. A61M 5/00
(52) U.S. Cl. ...................................... 604/110; 604/198
(58) Field of Search ................................ 604/110, 187, 604/192, 198, 263

(56) References Cited

U.S. PATENT DOCUMENTS

| | | | |
|---|---|---|---|
| 4,813,940 A | * | 3/1989 | Parry .......................... 604/198 |
| 5,222,945 A | | 6/1993 | Basnight |
| 5,232,457 A | | 8/1993 | Grim |
| 5,242,401 A | | 9/1993 | Colsky |
| 5,295,975 A | | 3/1994 | Lockwood, Jr. |
| 5,324,265 A | | 6/1994 | Murray et al. |
| 5,346,480 A | | 9/1994 | Hess et al. |
| 5,376,080 A | | 12/1994 | Petrussa |
| 5,389,085 A | | 2/1995 | D'Alessio |
| 5,403,286 A | | 4/1995 | Lockwood, Jr. |
| 5,591,138 A | | 1/1997 | Vaillancourt |
| 5,695,475 A | | 12/1997 | Best, Jr. |
| 6,379,336 B1 | | 4/2002 | Asbaghi et al. |
| 6,648,856 B1 | * | 11/2003 | Argento ...................... 604/192 |

* cited by examiner

Primary Examiner—Manuel Mendez
(74) Attorney, Agent, or Firm—Nydegger & Associates

(57) ABSTRACT

A safety device for protecting the needle of a blood collector includes a guard member that automatically covers the needle, after a blood collection procedure has been completed. Prior to the procedure, the guard member is restrained on the device in a proximal position to expose the needle, and to thereby facilitate the insertion of the needle into a vein of a patient. When a blood collection vial is engaged with the device, the guard member is released to move distally over the needle. Thus, after a procedure, and as the needle is being withdrawn from the patient, the guard member covers the needle to protect against subsequent inadvertent "sticks".

20 Claims, 2 Drawing Sheets

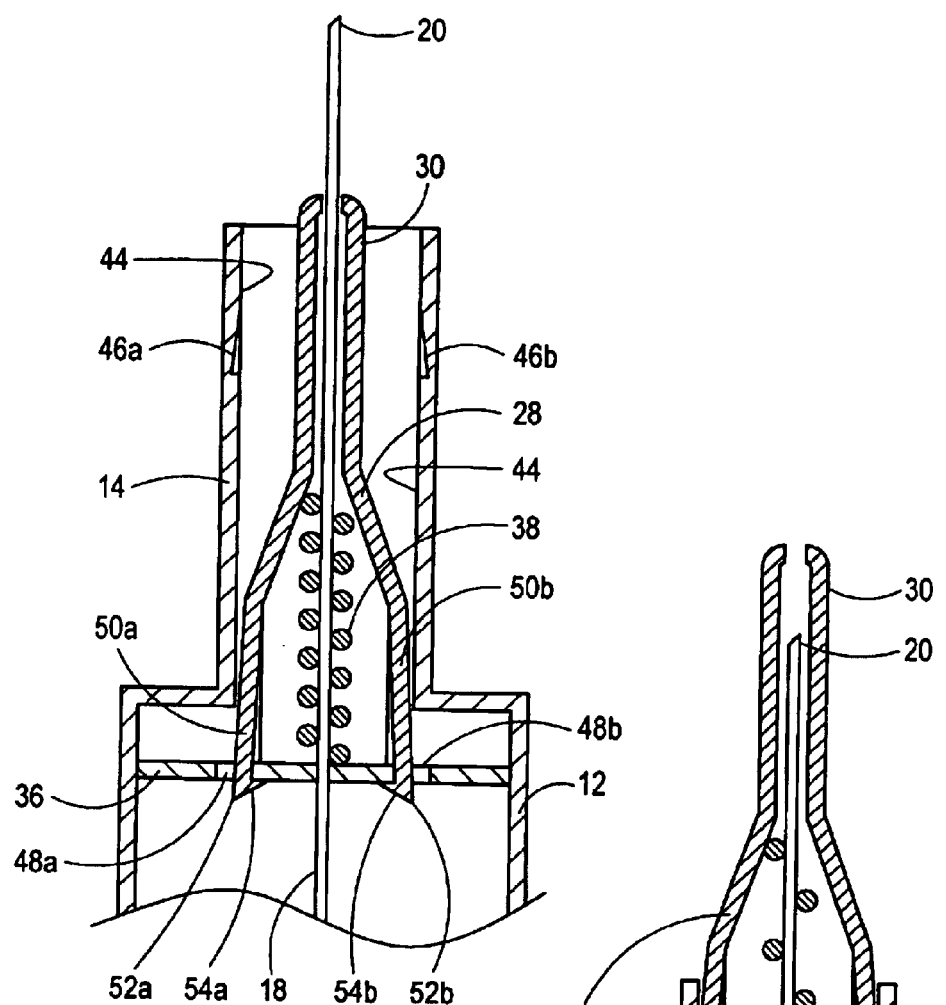
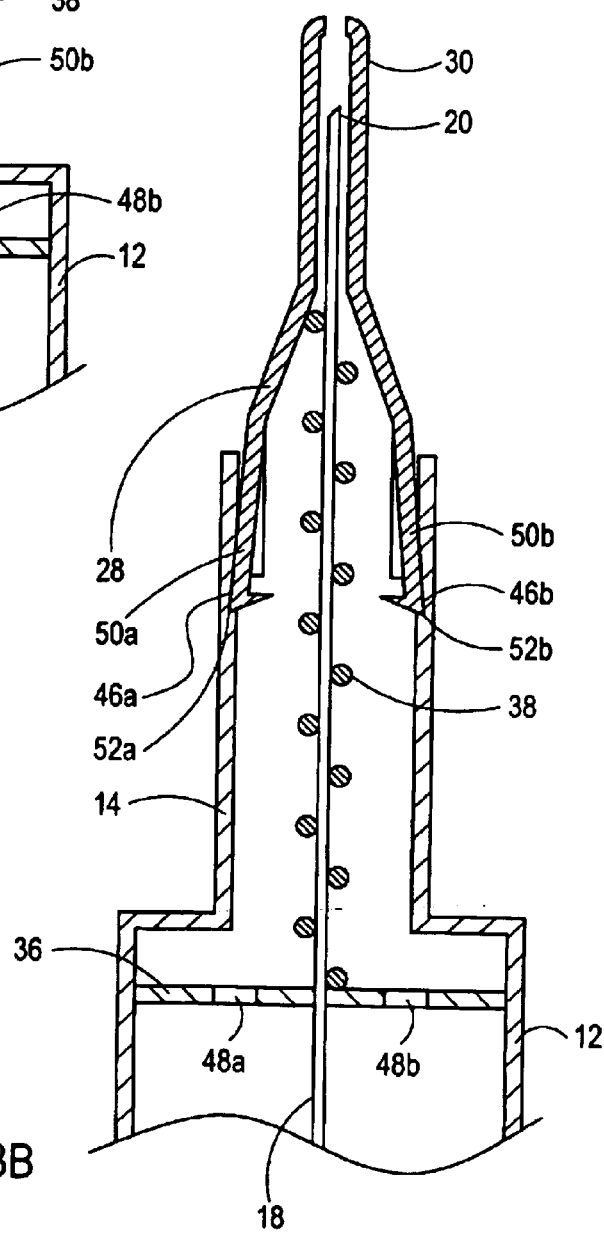
Fig. 3A
Fig. 3B

SAFETY DEVICE FOR BLOOD COLLECTION

FIELD OF THE INVENTION

The present invention pertains generally to devices and methods that are useful for collecting fluids. More particularly, the present invention pertains to devices and methods for collecting blood from a patient. The present invention is particularly, but not exclusively, useful for covering the needle of a blood collection device, to protect a user of the device against inadvertent or accidental "sticks," after a blood collection procedure has been performed.

BACKGROUND OF THE INVENTION

Inadvertent or accidental needle "sticks" are to be generally avoided in any situation. This is particularly so, however, for situations such as in clinical environments where needles are used for specific medical purposes, such as for the collection of blood. In such situations, the risk that contaminated body fluids (e.g. blood) may be transferred from one individual to another by a needle "stick," makes the prevention of such incidents extremely important.

In general, a typical blood collection procedure requires that a clinician somehow establish fluid communication with the vasculature of a patient. Normally this is accomplished by piercing the vein of the patient with a needle. Not surprisingly, this task requires a certain degree of skill. Moreover, the task of piercing a vein with a needle is greatly facilitated by being able to accurately and precisely position the tip of the needle against the patient. For this reason, exposed needle tips are typically used.

Prior to performing a blood collection procedure, as mentioned above, it is helpful to have an exposed needle tip. At this point in the procedure, the needle tip is, or at least should be, sterilized. Therefore, although unwanted and probably somewhat uncomfortable, an inadvertent or accidental "stick" does not pose a serious health risk. After the procedure has been completed, however, this is not the case. Instead, an exercise of extreme caution against an inadvertent or accidental needle "stick" is absolutely essential.

During a blood collection procedure, as with any other procedure wherein a needle is inserted into a patient, and subsequently withdrawn, it is preferable that the forces exerted against body tissue be minimized. In the case of a needle insertion, it is desirable that interactive forces between the needle and body tissue be confined to forces that act in a generally axial direction along the length of the needle. Stated differently, the introduction of rotational or twisting forces against body tissue, as a needle is being inserted into or withdrawn from a patient, is to be avoided.

In light of the above, it is an object of the present invention to provide a device for protecting the needle that is used in a blood collection procedure from causing inadvertent or accidental "sticks" after the blood collection procedure has been completed. It is another object of the present invention to provide a device for preventing the needle that is used in a blood collection procedure from exerting unnecessary forces against the body tissue of a patient during the procedure. Yet another object of the present invention is to provide a device for protecting a needle after a blood collection procedure that is relatively easy to manufacture, is simple to use, and is comparatively cost effective.

SUMMARY OF THE INVENTION

In accordance with the present invention, a safety device for protecting a needle, after a blood collection procedure, includes two coaxially aligned, hollow cylinders. One of these cylinders is a base member. The other is a guideway that extends axially from the base member and has a smaller diameter than the base member. Structurally, the guideway has a wall with an inner surface that is formed with two diametrically opposed indentations. Also, the wall of the guideway is formed with two diametrically opposed slots that are substantially parallel to the axis and extend along the length of the guideway. Preferably, the slots are in a plane that is generally perpendicular to a plane containing the indentations.

A disk-shaped retainer is attached to the device inside the base member, and is oriented generally perpendicular to the longitudinal axis of the base member. The needle is mounted on the retainer. For purposes of the present invention, the needle is straight, and it has piercing points at each of its ends. Also, as mounted on the retainer, the needle is aligned along the axis inside the base member, with the proximal end of the needle surrounded and protected by the base member. The needle is also aligned along the axis through the guideway. The distal end of the needle, however, extends beyond the guideway to a position where the distal point of the needle is at a distance from the guideway.

Along with the base member and the guideway, the device of the present invention also includes a guard member. This guard member surrounds the needle and, specifically, it is mounted on the device for axial movement over the needle, and through the guideway, from a proximal position to a distal position. Importantly, the guard member is selectively held in both its proximal and distal positions. To accomplish this, the guard member is formed with a pair of flexible extension arms, as well as a pair of protuberances.

In detail, each flexible extension arm is generally oriented axially on the device, and each has a detached proximal end that flexes radially outwardly from the axis. Structurally, the proximal end of each flexible arm is formed with a hook and a point. When the guard member is in its proximal position, the hook of the flexible arm is engaged with the retainer. With the guard member in the proximal position, the distal end of the needle is exposed for the collection of blood. On the other hand, when the extension arms have been released from the retainer, the guard member is automatically moved to its distal position by a spring. Specifically, the spring is positioned between the retainer and the guard member, and is biased to urge the guard member from the proximal position to the distal position.

Once the guard member is in its distal position, the extension arms flex further away from the axis. This allows the points on the arms to engage with the indentation in the wall of the guideway. This engagement then prevents a subsequent movement of the guard member in the proximal direction. Importantly, when the guard member is in its distal position, with the extension arms engaged with respective indentations, the guard member completely covers the distal end of the needle and protects users against inadvertent or accidental "sticks".

Another important aspect of the present invention is the interaction between the protuberances on the guard member that are inserted into the slots in the guideway. As the guard member moves from its proximal position to its distal position, this interaction prevents a rotation of the guard member about the axis relative to the device. Further, the dimensions of the slot are engineered so that the guard member has limited travel in the distal direction. Specifically, the distal ends of the slots act as stops for the protuberances on the guard member that prevent the spring from driving the guard member any further in a distal direction.

In operation, the distal end of the needle of the device is used to pierce into a vein of a patient for the purposes of collecting blood. The proximal end of the needle is then engaged in fluid communication with a blood collection vial. During this engagement of the blood collection vial with the device, the vial is urged against the proximal ends of the flexible arms on the guard member. This causes the proximal ends of the flexible extension arms to move outwardly, in a radial direction, and to release the guard member from the retainer. Blood is then collected. During the collection of blood, the guard member is restrained from movement by its contact with the patient. As the needle is subsequently withdrawn from the patient, however, the now-released guard member is free to move from its proximal position to its distal position. During this withdrawal of the needle, the protuberances on the guard member interact with the slots on the guideway to prevent a rotation of the guard member that might otherwise induce unwanted forces on the body tissue of the patient. Upon complete withdrawal of the needle from the patient, the needle is completely covered by the guard member.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3A is a cross sectional view of the device of the present invention, with portions removed for clarity, as seen along the line 3—3 in FIG. 1, with the guard member of the device in its proximal position; and FIG. 3B is a cross sectional view of the device of the present invention, with portions removed for clarity, as seen along the line 3—3 in FIG. 1, with the guard member of the device in its distal position.

DESCRIPTION OF THE PREFERRED EMBODIMENTS

Figure 1:
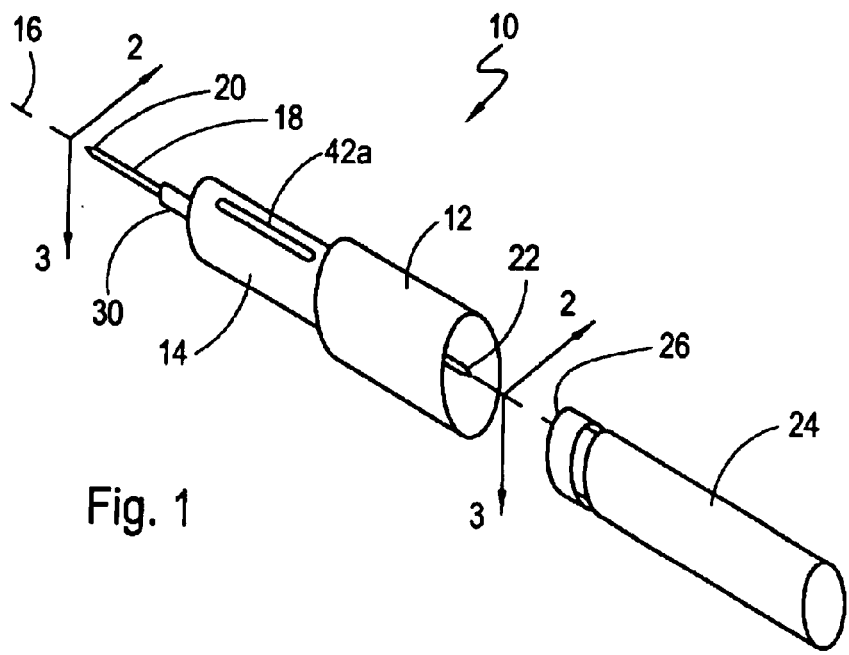
FIG. 1 is an exploded perspective view of the device of the present invention shown in operational proximity with a blood collection vial.

Referring initially to FIG. 1, a device in accordance with the present invention for use in a blood collection procedure is shown and generally designated 10. As shown, the device 10 includes a hollow, generally cylindrical shaped base member 12 and a hollow, generally cylindrical shaped guideway 14. Also, the base member 12 and guideway 14 are shown aligned coaxially along the axis 16, with the guideway 14 extending from the base member 12 in a distal direction. For reference purposes, the axis 16 shown in FIG. 1 is aligned with the respective longitudinal axes of the guideway 14 and the base member 12.

FIG. 1 also shows that the device 10 includes a substantially straight, hollow needle 18 that has both a distal tip 20 and a proximal tip 22. As shown, the needle 18 is aligned along the axis 16 with its proximal tip 22 positioned inside, and surrounded by, the base member 12. The distal tip 20, on the other hand, is shown extending from the device 10. This is done to facilitate inserting the distal tip 20 of the needle 18 into the vein of a patient (not shown) during a blood collection procedure. Still referring to FIG. 1 it can be appreciated that the device 10 of the present invention is intended for use with a blood collection vial 24. Specifically, the blood collection vial 24 is provided with a septum 26 that can be pierced by the proximal tip 22 of the needle 18 to establish fluid communication between the blood collection vial 24 and the needle 18.

Figure 2:
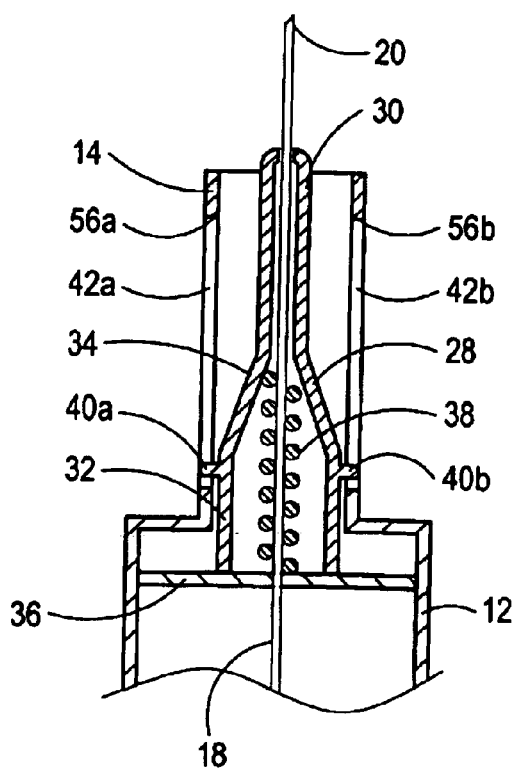
FIG. 2 is a cross sectional view of the device of the present invention, with portions removed for clarity, as seen along the line 2—2 in FIG. 1.

Referring now to FIG. 2 it is seen that the device 10 also includes a guard member 28 that is positioned generally inside the guideway 14 for movement along the axis 16. In detail, the guard member 28 has a substantially cylindrical shaped distal portion 30, a substantially cylindrical shaped proximal portion 32, and a tapered conical portion 34 that is located intermediate the distal portion 30 and the proximal portion 32. All of the portions 30, 32 and 34 of the guard member 28 are formed with respective lumen that allows the guard member 28 to effectively surround the needle 18. As will be better appreciated from the disclosure below, the distal portion 30 of guard member 28 is dimensioned to cover the distal tip 20 of needle 18, after a blood collection procedure has been completed.

Still referring to FIG. 2, it is seen and appreciated that a disk shaped retainer 36 is fixedly mounted in the device 10. Specifically, the retainer 36 is mounted inside the base member 12 in a plane that is substantially perpendicular to the axis 16, and it is fixed so as not to move relative to the base member 12. In addition to its other functions, an important function of the retainer 36 is that it fixedly holds the needle 18 substantially in alignment with the axis 16. Also, the retainer 36 provides a platform for the spring 38 that is positioned inside the guard member 28. In particular, the spring 38 is positioned inside the proximal portion 32 of base member 12 to create forces against both the retainer 36 and the tapered conical portion 34 of the guard member 28. As intended for the present invention, these forces urge the guard member 28 in a distal direction through the guideway 14. FIG. 2 also shows that the guard member 28 is formed with diametrically opposed protuberances 40a and 40b. Further, FIG. 2 shows that the guideway 14 is formed with diametrically opposed slots 42a and 42b that respectively receive the protuberances 40a and 40b. Thus, the interaction between the protuberances 40a and 40b and the slots 42a and 42b stabilizes and restricts the movement of guard member 28 relative to guideway 14 to only an axial translational motion. The pair of protuberances 40a,b and the pair of slots 42a,b are only exemplary, as the number of interactive protuberances and slots is essentially a matter of design choice.

Referring now to FIG. 3A it will be seen that the inner surface 44 of the guideway 14 is formed with diametrically opposed indentations 46a and 46b. Also it will be seen that the retainer 36 is formed with diametrically opposed holes 48a and 48b. Further, this view also shows that the guard member 28 includes diametrically opposed flexible extension arms 50a and 50b. More specifically, the flexible arms 50a and 50b extend from the guard member 28 in a generally proximal direction with their respective proximal ends formed with respective points 52a and 52b and respective hooks 54a and 54b. Importantly, the flexible extension arms 50a and 50b have an unstressed orientation relative to the axis 16. Due to the flexibility of the extension arms 50a and 50b, however, they will be biased toward this unstressed orientation whenever they are moved either inwardly or outwardly in a radial direction from the axis 16.

As intended for the present invention, when the guard member 28 is in its proximal position (FIG. 3A), the hooks 54a and 54b of flexible extension arms 50a and 50b, extend through the holes 48a and 48b of the retainer 36. In this position, the flexible extension arms 50a and 50b are positioned radially outward from their unstressed orientation. Accordingly, in this position they are biased toward the axis 16 to engage with the retainer 36, as shown, and thus they hold the guard member 28 in its proximal position. Also, in this proximal position, the guard member 28 is held on the retainer 36, against the action of the compressed spring 38. When the flexible extension arms 50a and 50b are released from the retainer 36, however, the guard member 28 is urged by the spring 38 into its distal position (FIG. 3B).

As the guard member 28 moves from its proximal position and into its distal position, the flexible extension arms 50a and 50b are forced by the inner surface 44 of guideway 14 radially inward from their unstressed orientation. Thus, as the guard member 28 moves through guideway 14 toward its distal position, the flexible extension arms 50a and 50b are biased to flex radially outward. This action then engages the points 52a and 52b of the arms 50a and 50b into respective indentation 46a and 46b when the guard member 28 reaches its distal position (FIG. 3B). Also, as the guard member 28 reaches its distal position, the protuberances 40a and 40b are positioned respectively against the distal ends 56a and 56b of the slots 42a and 42b to prevent further distal movement of the guard member 28. The consequence here is that the guard member 28 is held in its distal position, and prevented from moving either proximally or distally, while covering the distal tip 20 of needle 18 with the distal portion 30 of guard member 28.

In the operation of the device 10 of the present invention, after the distal tip 20 of needle 18 has been inserted into the vein of a patient, the blood collection vial 24 is engaged with the device 10. More specifically, this is accomplished by piercing the septum 26 of the vial 24 with the proximal tip 22 of the needle 18. With this engagement, fluid communication is established between the patient (not shown) and the blood collection vial 24 via the needle 18 of device 10. As this is being done, the device 10 is configured with the guard member 28 in its proximal position (FIG. 3A).

As the blood collection vial 24 is being engaged with the device 10, it happens that the septum 26 of vial 24 is urged against the hooks 54a and 54b of the flexible extension arms 50a and 50b. This forces the respective extension arms 50a and 50b to flex radially outward and away from the axis 16. This action, in turn, causes the hooks 54a and 54b to clear the holes 48a and 48b of the retainer 36, and to thereby release the guard member 28 from its proximal position. Initially, although the spring 38 is biased to drive the guard member 28 in a distal direction along the axis 16, the reaction of the patient against the distal portion 30 of the guard member 28 will restrain this movement.

After a blood collection procedure has been completed, the needle 18 is withdrawn from the patient. The guard member 28, now being released from its proximal position and free from the reaction force of the patient, will move under the influence of the spring 38 in a distal direction along the axis 16 over the needle 18. This movement continues until the guard member 28 reaches its distal position on the device 10 (FIG. 3B). As indicated above, when the guard member 28 is in its distal position, the points 52a and 52b of extension arms 50a and 50b engage with the indentations 46a and 46b. This engagement will then prevent any subsequent movement of the guard member 28 in a proximal direction. At the same time, the interaction between protuberances 40a and 40b on guard member 28 and the slots 42a and 42b of guideway 14 will prevent further movement of the guard member 28 in a distal direction. The result is that the distal portion 30 of guard member 28 covers the distal tip 20 of needle 18, and thereby prevents inadvertent or accidental "sticks" before the device 10 is properly discarded.

While the particular Safety Device for Blood Collection as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A safety device for protecting a needle after a blood collection procedure, which comprises:

a base member defining an axis;

a guideway extending axially from said base member, said guideway having a wall with an inner surface formed with at least one indentation;

a retainer attached to said base member, with the needle mounted on said retainer for alignment thereof along said axis; and a guard member formed with a flexible extension arm, said guard member being mounted on said device for axial movement over the needle between a proximal position wherein said extension arm is engaged with said retainer to expose the needle for collection of blood, and a distal position wherein said extension arm is engaged with said indentation to cover and protect said needle with said guard member.

2. A device as recited in claim 1 further comprising a spring positioned between said retainer and said guard member, said spring being biased to urge said guard member from the proximal position to the distal position.

3. A device as recited in claim 1 wherein said guard member is formed with a protuberance and said guideway is formed with at least one axially aligned slot for receiving said protuberance therein to prevent a rotation of said guard member relative to said guideway as said guideway moves from the proximal position to the distal position.

4. A device as recited in claim 3 wherein said guard member is formed with a plurality of flexible extension arms and a plurality of protrusions, and said guideway is formed with a respective plurality of indentations and slots.

5. A device as recited in claim 1 wherein the needle has a proximal end and a distal end, with said proximal end of the needle being engageable in fluid communication with a blood collection vial, and further wherein said proximal end of said flexible extension arm is outwardly moveable in a radial direction to release said guard member from said retainer in response to contact with the blood collection vial when the vial is engaged with the needle.

6. A device as recited in claim 5 wherein said flexible extension arm has a detached proximal end and said proximal end is formed with a hook and a point, said hook being engageable with said retainer and said point being engageable with said indentation.

7. A device as recited in claim 1 wherein said base member and said guideway are cylindrical shaped.

8. A fluid collection device which comprises:

a needle having a proximal end and a distal end;

a base member attached to said needle between the distal and proximal ends thereof to hold said needle in alignment along an axis relative to said base member;

a guard member slidingly mounted on said base member for movement along the axis, said guard member being selectively held in a first position relative to said base member to expose the distal end of said needle for use in a fluid collection procedure; and a means engageable in fluid communication with the proximal end of said needle for releasing said guard member from the first position for movement distally along the axis to a second position wherein said needle is protectively covered by said guard member.

9. A device as recited in claim 8 wherein said releasing means is a fluid vial.

10. A device as recited in claim 8 wherein said guard member is formed with a flexible extension arm and said device further comprises:

a guideway extending axially from said base member, said guideway having a wall with an inner surface formed with at least one indentation; and a retainer mounted on said base member and attached to said needle to hold said needle in alignment, wherein the flexible arm of said guard member is selectively engageable with said retainer to hold said guard member in the first position, and wherein the flexible arm of said guard member is engageable with the indentation to hold said guard member in the second position.

11. A device as recited in claim 10 wherein said guard member is formed with a protuberance and said guideway is formed with at least one axially aligned slot for receiving said protuberance therein to prevent a rotation of said guard member relative to said guideway as said guideway moves from the first position to the second position.

12. A device as recited in claim 11 wherein said guard member is formed with a plurality of flexible extension arms and a plurality of protrusions, and said guideway is formed with a respective plurality of indentations and slots.

13. A device a recited in claim 10 further comprising a spring positioned between said retainer and said guard member, said spring being biased to urge said guard member from the proximal position to the distal position.

14. A device a recited in claim 13 wherein said guard member comprises:

a substantially cylindrical shaped distal portion formed with a lumen;

a substantially cylindrical shaped proximal portion formed with a lumen; and a hollow conical shaped intermediate portion formed with a lumen, said intermediate portion being positioned between said distal portion and said proximal portion and having a taper with decreasing diameter in a distal direction, and wherein said needle extends through said respective lumens of said proximal portion, said intermediate portion and said distal portion.

15. A device as recited in claim 14 wherein said spring urges against said intermediate portion.

16. A method for protecting a needle after a blood collection procedure, which comprises the steps of:

providing a device comprising a base member defining an axis, a guideway extending axially from the base member with the guideway having a wall with an inner surface formed with at least one indentation, a retainer attached to the base member with the needle mounted on said retainer for alignment along the axis, the needle having a distal end and a proximal end, a guard member formed with a flexible extension arm mounted on the device for axial movement over the needle between a proximal position wherein the extension arm is engaged with said retainer to expose the distal end of the needle for collection of blood, and a distal position wherein the extension arm is engaged with the indentation to cover the distal end of the needle and protect the needle;

inserting the exposed distal end of the needle into a patient for blood collection; and engaging a blood collection vial in fluid communication with the proximal end of the needle to release the extension arm of the guard member from the retainer for distal movement of the guard member over the needle into its distal position.

17. A method as recited in claim 16 further comprises the step of using a spring positioned between the retainer and the guard member to urge the guard member from its proximal position to its distal position.

18. A method as recited in claim 17 wherein the guard member is formed with a protuberance and the guideway is formed with at least one axially aligned slot for receiving the protuberance therein to prevent a rotation of the guard member relative to the guideway as the guideway moves from the proximal position to the distal position.

19. A method as recited in claim 18 wherein the guard member is formed with a plurality of flexible extension arms and a plurality of protrusions, and the guideway is formed with a respective plurality of indentations and slots.

20. A method as recited in claim 19 wherein the base member and the guard member are substantially cylindrical shaped.

* * * * *